United States Patent
Jakobsson et al.

(10) Patent No.: US 7,067,296 B2
(45) Date of Patent: Jun. 27, 2006

(54) METHODS AND MEANS FOR MODULATING PGE SYNTHASE ACTIVITY

(75) Inventors: Per-Johan Jakobsson, Stockholm (SE); Bengt Samuelsson, Diursholm (SE); Ralf Morgenstern, Stockholm (SE); Anthony Ford-Hutchinson, Doylestown, PA (US); Joseph Mancini, Kirkland (CA)

(73) Assignee: Karolinska Innovations AB, Stockholm (SE)

( * ) Notice: Subject to any disclaimer, the term of this patent is extended or adjusted under 35 U.S.C. 154(b) by 652 days.

(21) Appl. No.: 10/109,438

(22) Filed: Mar. 28, 2002

(65) Prior Publication Data

US 2003/0064493 A1 Apr. 3, 2003

Related U.S. Application Data

(62) Division of application No. 09/433,466, filed on Nov. 4, 1999, now Pat. No. 6,395,502.
(60) Provisional application No. 60/107,687, filed on Nov. 9, 1998.

(51) Int. Cl.
*C12N 9/04* (2006.01)
*C12N 9/02* (2006.01)
*C12N 9/00* (2006.01)
*C07K 1/00* (2006.01)

(52) U.S. Cl. .................. 435/190; 435/183; 435/189; 530/350

(58) Field of Classification Search .................. 435/190, 435/189, 183, 195; 530/350
See application file for complete search history.

(56) References Cited

U.S. PATENT DOCUMENTS 6,432,640 B1 * 8/2002 Polyak et al. .................. 435/6

FOREIGN PATENT DOCUMENTS

WO    WO 9914356    3/1999

OTHER PUBLICATIONS

Polyak et al., Nature, 1997, 398, 300–305.*

Kornelia Polyak, et al. A model for p53–induced apoptosis. Letters to Nature (Sep. 18, 1997) 389:300–305.

D.R. Shalinsky et al. Inhibition of GSH–dependent PGH2 isomerase in mammary adenocarcinoma cells by allicin. PubMEd Query. (1989) p. 1.

Toshiya Ogorochi, et al. Purification and Properties of Prosaglandin H–E Isomerase from the Cytosol of Human Brain: Identification as Anionic Forms of Glutathione S–Transferase. Journal of Neurochemistry (1987) 48:900–909.

Yasuhito Tanaka et al. Immunochemical and Kinetic Evidence for Two Different Prostaglandin H–Prostaglandin E Isomerase in Sheep Vesicular Gland Microsomes . . . Journal of Biological Chemistry (Jan. 25, 1987) 262: 1374–1381.

Kikuko Watanabe et al. Two Types of Microsomal Prostaglandin E Synthase: Glutathione–Dependent and –Independent Prostaglandin E Synthases. Biochemical and Biophysical Research Communications (1997) 235: 148–152.

Per–Johan Jakobsson et al. Identification of Human, prostaglandin E synthase: A microsomal, potential novel drug target. Proc. Nat l. Acad. Sci.(1999) 96:7220–7225.

XP–002132552 1 Sheet of Sequence.

* cited by examiner

*Primary Examiner*—Maryam Monshipouri
(74) *Attorney, Agent, or Firm*—Dann, Dorfman, Herrell and Skillman

(57) ABSTRACT

Isolated PGE synthase, provided from encoding nucleic acid. Methods of production and use. Assays for modulators, especially inhibitors, of PGE synthase activity.

5 Claims, 3 Drawing Sheets

Figure 1
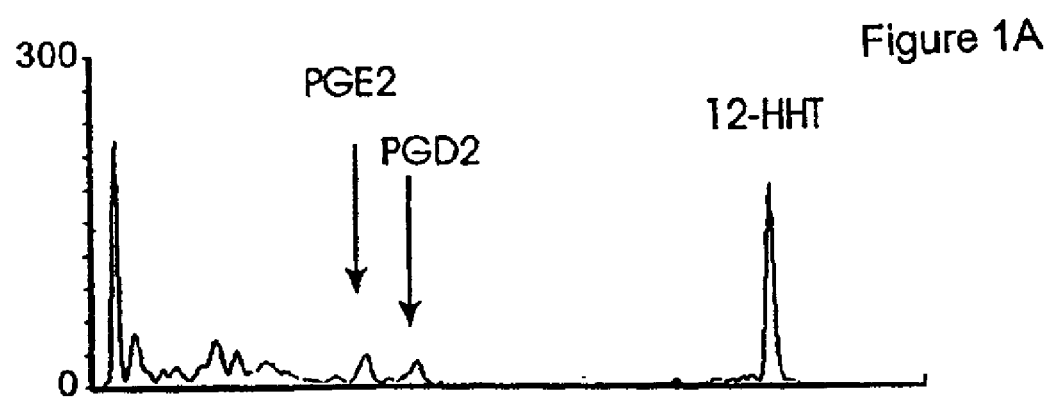
Figure 1A
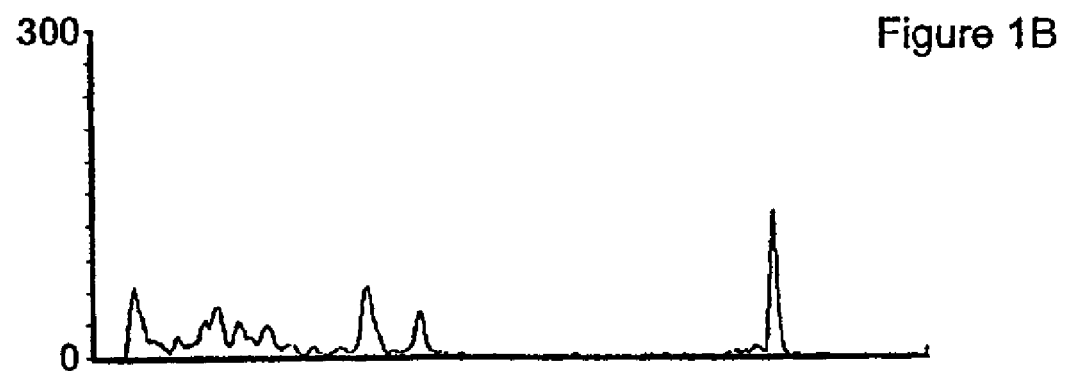
Figure 1B
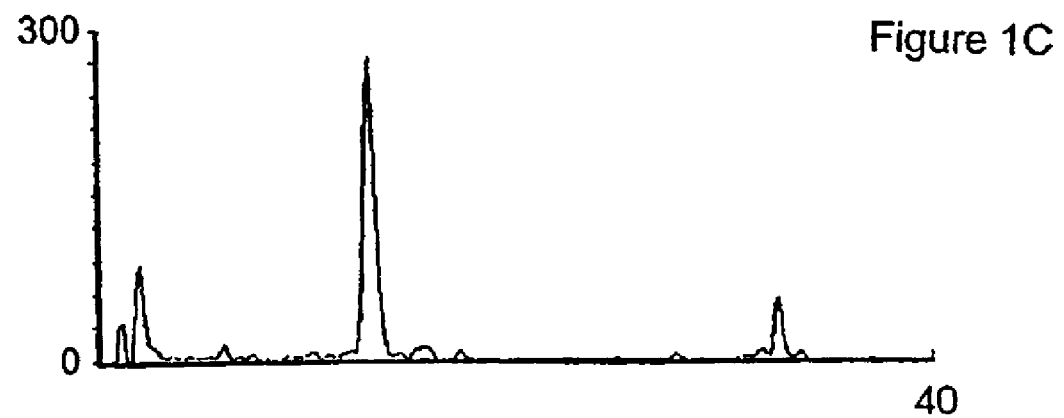
Figure 1C

SEQUENCE LISTING

```
<160> NUMBER OF SEQ ID NOS: 5

<210> SEQ ID NO 1
<211> LENGTH: 459
<212> TYPE: DNA
<213> ORGANISM: Homo sapiens

<400> SEQUENCE: 1
atgcctgccc acagcctggt gatgagcagc ccggccctcc cggccttcct gctctgcagc        60
acgctgctgg tcatcaagat gtacgtggtg gccatcatca cgggccaagt gaggctgcgg       120
aagaaggcct tgccaaccc cgaggatgcc ctgagacacg gaggccccca gtattgcagg        180
agtgaccccg acgtggaacg ctgcctcagg gcccaccgga acgacatgga gaccatctac       240
cccttccttt tcctgggctt cgtctactcc tttctgggtc ctaacccttt tgtcgcctgg       300
atgcacttcc tggtcttcct cgtgggccgt gtggcacaca ccgtggccta cctggggaag       360
ctgcgggcac ccatccgctc cgtgacctac acctggccc agctccctg cgcctccatg       420 gctctgcaga tcctctggga agcggcccgc cacctgtga                             459

<210> SEQ ID NO 2
<211> LENGTH: 152
<212> TYPE: PRT
<213> ORGANISM: Homo sapiens

<400> SEQUENCE: 2

Met Pro Ala His Ser Leu Val Met Ser Ser Pro Ala Leu Pro Ala Phe
  1               5                  10                  15

Leu Leu Cys Ser Thr Leu Leu Val Ile Lys Met Tyr Val Val Ala Ile
             20                  25                  30

Ile Thr Gly Gln Val Arg Leu Arg Lys Lys Ala Phe Ala Asn Pro Glu
         35                  40                  45

Asp Ala Leu Arg His Gly Gly Pro Gln Tyr Cys Arg Ser Asp Pro Asp
     50                  55                  60

Val Glu Arg Cys Leu Arg Ala His Arg Asn Asp Met Glu Thr Ile Tyr
 65                  70                  75                  80
```

```
Pro Phe Leu Phe Leu Gly Phe Val Tyr Ser Phe Leu Gly Pro Asn Pro
                85                  90                  95

Phe Val Ala Trp Met His Phe Leu Val Phe Leu Val Gly Arg Val Ala
               100                 105                 110

His Thr Val Ala Tyr Leu Gly Lys Leu Arg Ala Pro Ile Arg Ser Val
           115                 120                 125

Thr Tyr Thr Leu Ala Gln Leu Pro Cys Ala Ser Met Ala Leu Gln Ile
       130                 135                 140

Leu Trp Glu Ala Ala Arg His Leu
145                 150

<210> SEQ ID NO 3
<211> LENGTH: 16
<212> TYPE: PRT
<213> ORGANISM: Homo sapiens

<400> SEQUENCE: 3

Cys Arg Ser Asp Pro Asp Val Glu Arg Ser Leu Arg Ala His Arg Asn
  1               5                  10                  15

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 4
gagagacata tgcctgccca cagcctg                                              27

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 5
gagagaaagc ttcacaggtg gcgggccgc                                            29
```

METHODS AND MEANS FOR MODULATING PGE SYNTHASE ACTIVITY

This application is a divisional of U.S. Pat. application Ser. No. 09/433,466, filed Nov. 4, 1999, now U.S. Pat. No. 6,395,502, which claims priority under 35 U.S.C. §119(e) to U.S. Provisional Application 60/107,687 filed Nov. 9, 1998.

The present invention relates to modulating PGE synthase activity. In particular, the present invention is based on identification of PGE synthase and DNA encoding it, providing for assays for substances able to modulate, especially inhibit, PGE synthase activity. PGE is a potent compound known to produce inflammation (symptoms including fever and pain), and inhibition of its production may be used in treatment of inflammation, arthritis, cancer, Alzheimer's disease, in modulating apoptosis, and treating pain.

Prostaglandin endoperoxide $H_2$ ($PGH_2$) is formed from arachidonic acid by the action of cyclooxygenase (cox) -1 or -2. Cox-1 is constitutively expressed in many cells and tissues such as platelets, endothelium, stomach and kidney whereas the cox-2 protein can be induced by proinflammatory cytokines like interleukin-1β at sites of inflammation. For recent reviews on cox see Smith, W. (1997) Advances in Experimental Medicine & Biology 400B, 989–1011; Herschman, H. R. (1996) Biochimica et Biophysica Acta 1299, 125–40; Dubois, R., et al.(1998) Faseb J. 12, 1063–1073. Downstream of the cyclooxygenases, their product $PGH_2$ can be further metabolized into the various physiologically important eicosanoids e.g. $PGF_{2\alpha}$, $PGE_2$, $PGD_2$, $PGI_2$ (prostacyclin) and thromboxane (TX) $A_2$ (Smith, W. L. (1992) Am. J. Physiol. 263, F181–F191).

The mechanism for the biosynthesis of $PGE_1$ and $PGF_{1\alpha}$ (formed using dihomo-γ-linolenic acid instead of arachidonic acid) (Hamberg, M. & Samuelsson, B. (1967) J. Biol. Chem. 242, 5336–5343) by sheep vesicular glands was postulated to proceed via a cyclic endoperoxide (Samuelsson, B. (1965) J. Am. Chem. Soc. 87, 3011–3013) later designated PGH2 (Hamberg, M. & Samuelsson, B. (1973) Proc. Natl. Acad. Sci. USA 70, 899–903; Hamberg, M., et al. (1974) Proc. Natl. Acad. Sci. USA 71, 345–349; Nugteren, D. H. & Hazelhof, E. (1973) Biochim. Biophys. Acta 326, 448–461). In short, the reactions catalyzed by the cyclooxygenases involve a stereospecific abstraction of the 13-pro-S hydrogen atom from arachidonic acid. This leads to the formation of a carbon radical that is trapped by molecular oxygen at position C-11, formation of the 9,11-endoperoxide and the bond between the C-8 and C-12 positions with trans aliphatic side chains, radical rearrangement to C-15 and reaction with a second molecule of oxygen. In the next step the resulting peroxy group at C-15 is reduced to a hydroperoxy group and $PGG_2$ is formed. This hydroperoxy group can subsequently be reduced by the peroxidase activity of cyclooxygenase (in the presence of a reducing agent e.g. glutathione) thus forming $PGH_2$ The enzyme/s responsible for the isomerization of $PGH_2$ into $PGE_2$ are not well known. Attempts have been made to purify the microsomal PGE synthase from ovine and bovine seminal vesicles, an organ known to contain high PGE synthase activity (Ogino, N., et al. (1977) Journal of Biological Chemistry 252, 890–5; Moonen, P., et al. (1982) Methods in Enzymology 86, 84–91). These studies have shown that the microsomal PGE synthase can be solubilized and partly purified. The enzyme activity was also dependent on glutathione but rapidly inactivated during the course of purification. Two monoclonal antibodies designated IGG1(hei-7) and IGGl(hei-26) raised against partly purified PGE synthase from sheep seminal vesicles, could immunoprecipitate two proteins from sheep seminal vesicles with molecular masses of 17.5 and 180 kDa, respectively (Tanaka, Y., et al. (1987) J. Biol. Chem. 262, 1374–1381). Both these precipitated proteins were found to possess glutathione dependent PGE synthase activity but no glutathione S-transferase activity. Interestingly, the IGG1(hei-7) antibody also caused co-precipitation of cyclooxygenase, demonstrating that the 17.5 kDa protein and the cox proteins were on the same side of the microsomal membranes. The 17.5 kDa protein showed a Km for $PGH_2$ of 40 μM, similar to what has been described by others investigating the microsomal PGE synthase (Moonen, P., et al. (1982) Methods in Enzymology 86, 84–91). In contrast, the larger protein demonstrated a Km for $PGH_2$ of 150 μM. Additional proteins, belonging to the cytosolic glutathione S-transferase superfamily, have also been described to possess PGE, PGD and PGF synthase activities (Urade, Y., et al. (1995) J. Lipid Med. 12, 257–273). Recently, a microsomal 16.5 kDa protein was purified from sheep seminal vesicles possessing glutathione dependent $PGF_{2\alpha}$ synthase activity (Burgess, J. R. & Reddy, C. C. (1997) Biochem. & Mol. Biol. Int. 41, 217–226). The enzyme (prostaglandin endoperoxide reductase) could also catalyze the reduction of cumene hydroperoxide whereas, 1-chloro-2,4-dinitrobenzene (typical substrate for various glutathione S-transferases) was not a substrate. Microsomal PGE synthase activity was also measured in various rat organs (Watanabe, K., et al.(1997) Biochemical & Biophysical Research Communications 235, 148–52) and high glutathione dependent activity was found in the deferens duct, genital accessory organs and kidney. Glutathione independent microsomal PGE synthase activity was observed in heart, spleen and uterus.

The enzyme responsible for PGE biosynthesis therefore provides a novel target for drug development in order to treat various inflammatory disorders. However, as is apparent from the preceding discussion, no-one has previously succeeded in providing pure PGE synthase nor the means to provide it.

Oxford Biomedical sells a partially purified preparation of ovine PGE synthase (Catalog Number PE 02). Analysis of that preparation indicates it is rather crude, including a complex mixture of numerous components.

Particular difficulties in purifying PGE synthase include the fact that the protein is a membrane protein, in general very hard to purify to homogeneity and the fact that its enzyme activity is very unstable after solubilization. Also, the work described herein demonsrates that the protein possesses very high enzyme activity, providing indication that the amounts of protein are very low within cells, adding to the difficulty of purification.

Urade et al.(1995) J. Lipid Med. 12, 257–273, notes "little is known about the properties of PGE synthase". Even more recently, William Smith in "Molecular Biology of Prostanoid Biosynthetic Enzymes and Receptors", Advances in Experimental Medicine & Biology, 400B: 989–1011, published in 1997, noted "The PGE synthase story has been a perplexing one", pointing out that PGE formation has not been attributed to a unique protein.

The work of the present inventors described below demonstrates that human PGE synthase is a member of a protein superfamily consisting of membrane associated 14–18 kDa proteins involved in eicosanoid and glutathione metabolism. PGE synthase demonstrates 38% identity on the amino acid sequence level with microsomal glutathione S-transferase 1. The human cDNA sequence as well as the predicted amino acid sequence were deposited in 1997 in public databases under the name of MGST1-L1 (GenBank accession number AF027740) as well as a p53 induced PIG12 (GenBank accession number AF010316). No function has previously been ascribed to these cDNA sequences.

Polyak et al. (1997) *Nature* 389: 300–305 identified what they called "PIG12" by cloning sequences of which expression was upregulated by P53. They state "PIG12 is a novel member of the microsomal glutathione S-transferase family of genes", but identify not actual function. There is certainly no suggestion that their PIG12 was actually human PGE synthase.

In summary, no-one has previously provided PGE synthase in any form or quantity that would allow for amino acid sequencing to provide a potential starting point for attempted cloning of a coding sequence. Furthermore there was no suggestion that the sequence on the databases which the present inventors have now demonstrated to encode PGE synthase did actually encode PGE synthase.

In the light of the inventors' work, the present invention provides in various aspects for use of purified PGE synthase in various contexts, in particular in assays and screening methods for substances able to modulate, especially inhibit, PGE synthase activity. The purified PGE synthase may be made by recombinant expression from encoding nucleic acid. It may be expressed in eukaryotic or prokaryotic expression systems and may lack native glycosylation. Substances identified as modulators of PGE synthase may be employed in control or treatment of inflammation, arthritis, cancer or other cellular growth abnormality, Alzheimer's disease, in modulating apoptosis, and treating pain.

BRIEF DESCRIPTION OF THE FIGURES

FIG. 1 shows the results of reverse-phase HPLC chromatogram of the products formed after incubations with $PGH_2$ (plotting counts per minute (CPM) against time in minutes).

FIG. 1A shows results obtained with PGE synthase membrane fraction mixed with stop solution.

FIG. 1B shows results obtained with buffer.

FIG. 1C shows results obtained with PGE synthase membrane fraction. B and C were incubated for 2 min prior to addition of stop solution. Products were detected using radioactivity detection. The first 20 min represents isocratic elution using water, acetonitrile and trifluoroacetic acid (70:30:0.007, by vol) as mobile phase with a flow rate of 1 ml/min. Then a linear gradient was applied from 100% mobile phase to 100% methanol over a 10 min period, which was sustained for the rest of the run.

Figure 2:
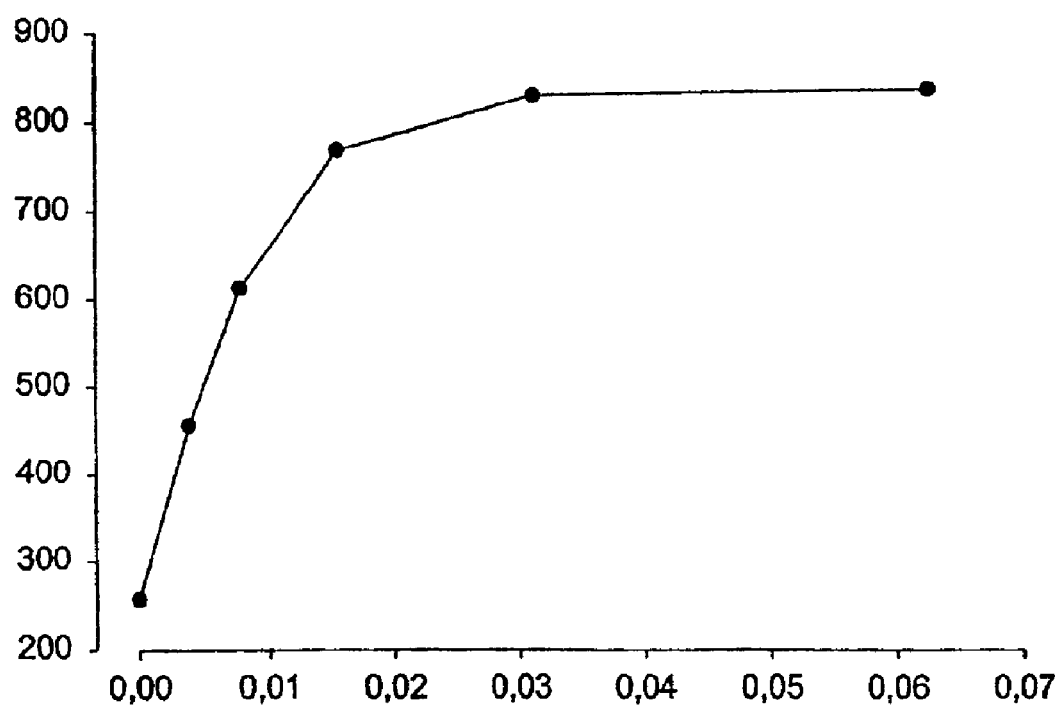
FIG. 2 illustrates dependency of $PGE_2$ formation on membrane protein concentration, amount of $PGE_2$ in pmol being plotted against mg/ml of the protein.

The following abbreviations are used herein:

$PGG_1$, Prostaglandin $G_1$: 15(S)-hydroperoxy-9α,11α-peroxidoprosta-13-enoic acid;

$PGG_2$, Prostaglandin $G_2$: 15(S)-hydroperoxy-9α,11α-peroxidoprosta-5-cis-13-trans-dienoic acid;

$PGG_3$, Prostaglandin $G_3$: 15(S)-hydroperoxy-9α,11α-peroxidoprosta-5,13,17-trienoic acid;

$PGH_1$, Prostaglandin $H_1$: 15(S)-hydroxy-9α,11α-peroxidoprosta-13-enoic acid;

$PGH_2$, Prostaglandin $H_2$: 15(S)-hydroxy-9α,11α-peroxidoprosta-5-cis-13-trans-dienoic acid;

$PGH_3$, Prostaglandin $H_3$: 15(S)-hydroxy-9α,11α-peroxidoprosta-5,13,17-trienoic acid;

$PGE_2$, Prostaglandin $E_2$: 11α,15(S)-dihydroxy-9-ketoprosta-5-cis-13-trans-dienoic acid;

$PGF_{2α}$, Prostaglandin $F_{2α}$: 9α,11α,15(S)-trihydroxyprosta-5-cis-13-trans-dienoic acid;

$PGD_2$, Prostaglandin $D_2$: 9α,15(S)-dihydroxy-11-ketoprosta-5-cis-13-trans-dienoic acid;

$PGI_2$, Prostacyclin: 6,9α-epoxy-11α,15(S)-dihydroxyprosta-5-cis-13-trans-dienoic acid;

$TXA_2$, Thromboxane $A_2$: 9α,11α,epoxy-15(S)-hydroxythromba-5-cis-13-trans-dienoic acid;

12-HHT: 12(S)-Hydroxy-8,10-trans-5-cis-heptadecatrienoic acid; PGH synthase: Prostaglandin H synthase;

RP-HPLC: Reverse-phase high performance liquid chromatography;

LT: Leukotriene;

$LTA_4$, Leukotriene $A_4$: 5(S)-trans-5,6-oxido-7,9-trans-11,14-cis-eicosatetraenoic acid;

$LTC_4$, Leukotriene $C_4$: 5(S)-hydroxy-6(R)-S-glutathionyl-7,9-trans-11,14-cis-eicosatetraenoic acid;

FLAP: 5-lipoxygenase activating protein;

MGST: microsomal glutathione S-tranferase;

NSAID: Nonsteroidal anti-inflammatory drugs.

The present invention provides pure PGE synthase. A preferred polypeptide of the invention includes the amino acid sequence of SEQ ID NO. 2.

Isolated polypeptides of the invention will be those as defined herein in isolated form, free or substantially free of material with which it is naturally associated such as other polypeptides with which it is found in the cell. The polypeptides may of course be formulated with diluents or adjuvants and still for practical purposes be isolated—for example the polypeptides will normally be mixed with gelatin or other carriers if used to coat microtitre plates for use in immunoassays. The polypeptides may be glycosylated, either naturally or by systems of heterologous eukaryotic cells, or they may be (for example if produced by expression in a prokaryotic cell) unglycosylated. The term "lacking native glycosylation" may be used with reference to a polypeptide which either has no glycosylation (e.g. following production in a prokaryotic cell) or has a pattern of glycosylation that is not the native pattern, e.g. as conferred by expression in a particular host cell type (which may be CHO cells).

Polypeptides of the invention may be modified for example by the addition of a signal sequence to promote their secretion from a cell or of histidine residues to assist their purification. Fusion proteins may be generated that incorporate (e.g.) six histidine residues at either the N-terminus or C-terminus of the recombinant protein. Such a histidine tag may be used for purification of the protein by using commercially available columns which contain a metal ion, either nickel or cobalt (Clontech, Palo Alto, Calif., USA). These tags also serve for detecting the protein using commercially available monoclonal antibodies directed against the six histidine residues (Clontech, Palo Alto, Calif., USA).

Polypeptides which are amino acid sequence variants, alleles, derivatives or mutants are also provided by the present invention, such forms having at least 70% sequence identity, for example at least 80%, 90%, 95%, 98% or 99% sequence identity to SEQ ID NO. 2. A polypeptide which is a variant, allele, derivative or mutant may have an amino acid sequence which differs from that given in SEQ ID NO. 2 by one or more of addition, substitution, deletion and insertion of one or more (such as from 1 to 20, for example 2, 3, 4, or 5 to 10) amino acids.

The amino acid sequence of SEQ ID NO. 2 is encoded by the human nucleotide sequence of SEQ ID NO. 1. Polypeptides of the invention include those encoded by alleles of the human sequence, and homologues of other mammals, particularly primates, as well as fragments of such polypeptides as discussed further below. The primary sequence of the PGE synthase protein will be substantially similar to that of SEQ ID NO. 2 and may be determined by routine techniques available to those of skill in the art. In essence, such techniques include using polynucleotides derived from SEQ ID NO. 1 as probes to recover and to determine the sequence of the PGE synthase gene in other species. A wide variety of techniques are available for this, for example PCR amplification and cloning of the gene using a suitable source of mRNA, or by methods including obtaining a cDNA library from the mammal, e.g a cDNA library from one of the above-mentioned sources, probing said library with a polynucleotide of the invention under stringent conditions, and recovering a cDNA encoding all or part of the PGE synthase protein of that mammal. Where a partial cDNA is obtained, the full length coding sequence may be determined by primer extension techniques.

An "active portion" of the polypeptides means a peptide which is less than said full length polypeptide, but which retains its essential biological activity. In particular, the active portion retains the ability to catalyse PGE synthesis from PGH in the presence of glutathione.

Suitable active portions thus include the central segment of SEQ ID NO. 2, e.g. between about residues 30–130. The relevant catalytic region of the PGE synthase protein is expected to be in the central segment of SEQ ID NO. 2 based on analogy with MGST1 and $LTC_4$ synthase: amino acids 1–41 can be removed from MGST1 by proteolysis without loss of function (Andersson et al., (1994) Biochim. Biophys. Acta 1204, 298–304); C-terminal segments can be exchanged between $LTC_4$ synthase and FLAP without alteration of protein function (Lam et al., (1997) J. Biol. Chem. 272, 13923–13928).

One active portion of the invention includes or consists of amino acids 30–152 of SEQ ID NO. 2. Another active portion includes or consists of amino acids 1–130 of SEQ ID NO. 2. A still further active portion includes or consists of amino acids 30–130 of SEQ ID NO. 2.

The present invention includes a polypeptide including an active portion of a PGE synthase provided herein, which polypeptide may include heterologous amino acids, such as an identifiable sequence or domain of another protein, or a histidine tag or other tag sequence, and the invention includes a polypeptide consisting essentially of an active portion of a PGE synthase.

A polypeptide according to the present invention may be isolated and/or purified (e.g. using an antibody) for instance after production by expression from encoding nucleic acid. Polypeptides according to the present invention may also be generated wholly or partly by chemical synthesis, for example in a step-wise manner. The isolated and/or purified polypeptide may be used in formulation of a composition, which may include at least one additional component, such as a diluent.

A polypeptide according to the present invention may be used in screening for molecules which affect or modulate its activity or function. Such molecules may be useful in a therapeutic (which may include prophylactic) context. This is discussed in detail below.

A polypeptide of the invention may be labelled with a revealing label. The revealing label may be any suitable label which allows the polypeptide to be detected. Suitable labels include radioisotopes, e.g. $^{125}I$, enzymes, antibodies, polynucleotides and linkers such as biotin.

As noted, a preferred way of producing a polypeptide of the invention is to employ encoding nucleic acid in a suitable expression system to produce the polypeptide recombinantly. In a further aspect the present invention provides the use of nucleic acid encoding PGE synthase polypeptide in production of PGE synthase.

Nucleic acids of the present invention include nucleic acids which include a sequence encoding a polypeptide which includes the amino acid sequence of SEQ ID NO. 2 and a polypeptide having at least 70% sequence identity to SEQ ID NO. 2. Preferably the degree of sequence identity in either case is at least 80%, such as at least 90%, 95%, 98% or 99%.

Nucleic acids useful in the invention further include nucleic acids which include a sequence having at least 70% homology, more preferably at least 80%, such as at least 90%, 95%, 98% or 99% sequence homology to the nucleic acid sequences of SEQ ID NO. 1 or its complement.

Nucleic acid of the invention may encode the amino acid sequence of SEQ ID NO. 2, in which case it may include SEQ ID NO. 1 or a different nucleotide sequence, as permitted by degeneracy of the genetic code, or a polypeptide with PGE synthase activity which has an amino acid sequence which differs from SEQ ID NO. 2.

Where an aspect of the present invention is expressed in terms of nucleic acid with at least a specified % homology with SEQ ID NO. 1 or its complement, the actual sequence of SEQ ID NO. 1 or its complement may be excluded. In various embodiments the present invention provides non-naturally occurring nucleic acid encoding a polypeptide PGE synthase activity, such as a polypeptide including the amino acid sequence of SEQ ID NO. 2 or an allelic variant thereof, or a non-naturally occurring polypeptide mutant, variant or derivative thereof.

Nucleic acid sequences encoding all or part of a PGE synthase gene can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) preparing cDNA sequences. Modifications to the wild type sequences described herein can be made, e.g. using site directed mutagenesis, to lead to the expression of modified polypeptides or to take account of codon preference in the host cells used to express the nucleic acid.

In general, short sequences for use as primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15–50 nucleotides) based on the sequence information provided herein to a region of the mRNA or genomic sequence encoding the mRNA which it is desired to clone, bringing the primers into contact with mRNA or cDNA obtained from mammalian cells (which may for example be any of the human cell line A549, epithelial cells, osteosarcoma derived cell lines, osteoblasts, human leukocytes, fibroblasts, endothelial cells, cells of the reproductive system, mesangial cells and other kidney cells), performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the sequences described herein. Genomic clones containing the PGE synthase gene and its introns and promoter regions may also be obtained in an analogous manner, starting with genomic DNA from a mammalian, e.g. human cell, e.g. a primary cell such as a liver cell, a tissue culture cell or a library such as a phage, cosmid, YAC (yeast artificial chromosome), BAC (bacterial artificial chromosome) or PAC (P1/P2 phage artificial chromosome) library.

Polynucleotides which are not 100% homologous to the sequences of the present invention but fall within the scope of the invention can be obtained in a number of ways.

Other human variants (for example allelic forms) of the PGE synthase gene described herein may be obtained for example by probing cDNA or genomic DNA libraries made from human tissue.

In addition, other animal, and particularly mammalian (e.g. mouse, rat or rabbit, sheep, goat, cow, horse, pig, dog, cat, or primate) homologues of the gene may be obtained. Such sequences may be obtained by making or obtaining cDNA libraries made from dividing cells or tissues or genomic DNA libraries from other animal species, and probing such libraries with probes including all or part of a nucleic acid of the invention under conditions of medium to high stringency (for example for hybridization on a solid support (filter) overnight incubation at 42° C. in a solution containing 50% formamide, 5×SSC (750 mM NaCl, 75 mM sodium citrate), 50 mM sodium phosphate (pH 7.6), 5×Denhardt's solution, 10% dextran sulphate and 20 µg/ml salmon sperm DNA, followed by washing in 0.03 M sodium chloride and 0.03 M sodium citrate (i.e. 0.2×SSC) at from about 50° C. to about 60° C.).

Thus the present invention may employ an isolated nucleic acid which hybridizes to the nucleotide sequence set forth in SEQ ID NO. 1 under the abovementioned hybridization and washing conditions. Such a nucleic acid is suitable for use as a probe for detecting the a PGE synthase gene, for example in Southern blots or in metaphase spreads.

Alternatively, such polynucleotides may be obtained by site directed mutagenesis of the sequences of SEQ ID NO. 1 or allelic variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides. Further changes may be desirable to represent particular coding changes which are required to provide, for example, conservative substitutions.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

Preferably, a polynucleotide of the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, phagemid or baculoviral, cosmids, YACs, BACs, or PACs as appropriate.

The vectors may be provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in methods of gene therapy. Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others.

For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Vectors may be transformed into a suitable host cell as described above to provide for expression of a polypeptide of the invention. Thus, in a further aspect the invention provides a process for preparing polypeptides according to the invention which includes cultivating a host cell transformed or transfected with an expression vector as described above under conditions to provide for expression by the vector of a coding sequence encoding the polypeptides, and recovering the expressed polypeptides. Polypeptides may also be expressed in in vitro systems, such as reticulocyte lysate.

Following production of a polypeptide of the invention it may be tested for PGE synthase activity, e.g. by determination of PGE production on incubation of the polypeptide with $PGH_2$ and reduced glutathione. PGE can be detected using Reverse-phase high pressure liquid chromatography (R-P HPLC) which allows for quantitation of the amount present.

Isolated/pure PGE synthase may be used in a variety of contexts.

Because of the importance of PGE in inflammation and other contexts of medical significance, important aspects of the invention are concerned with identifying substances which are able to affect PGE production, in particular by modulating PGE synthase activity. Of most interest is the inhibition of FGE synthase activity to reduce levels of PGE production.

PGE is well known to cause pain both in vivo and in vitro (Bley et al. (1998) Trends in Pharmacological Sciences 19, 141–147). The prostaglandin E receptor ($EP_3$) has also been demonstrated to be crucial for functional fever response (Ushikubi et al (1998) Nature 395, 281–284). The role of prostaglandins in inflammation and inflammatory diseases such as arthritis has also been well documented through the use of various cyclooxygenase inhibitors (nonsteroidal antioinflammatory drugs, NSAIDs, including aspirin (Vane & Botting (1998) American J. of Med. 104(3A), 2S–8S). In this respect, PGE has been recognized as the most potent proinflammatory prostaglandin (Moncada et al. (1973) Nature 246, 217–9), which is which specific removal of this compound by inhibition of PGE synthase may be used to provide control of inflammatory reaction with fewer side effects in comparison with the presently used NSAIDs.

Several reports have demonstrated significant anti-tumour effects by NSAIDs on colorectal cancer (Giovannucci et al. (1994) Annals of Internal Medicine 121, 241–6; Giardiello et al, (1995) European Journal of Cancer 31A, 1071; Williams et al (1997) Journal of Clinical investigation 100, 1325–9). PGE promotes cancer cell proliferation (Qiao et al (1995) Biochimica et Biophysica Acta 1258, 215–23) as well as inhibiting programmed cell death (Ottonello et al (1998) Experimental Hematology 26, 895–902; Goetzl et al (1995) Journal of Immunology 154, 1041–7), overall resulting in support of cancer cell growth (Sheng et al (1998) Cancer Research 58, 362–6). Inhibition of PGE formation thus leads to slower proliferation in combination with increased apoptosis of the cancer cell population. This inhibiting effect of NSAIDs has also been observed in other cancer conditions such as non-small cell lung cancer (Hida et al. (1998) Anticancer Research 18, 775–82).

Prostaglandins have also been implicated in Alzheimer's disease. Several clinical trials have demonstrated that users of NSAIDs experience as little as one half of the risk of acquiring Alzheimer's disease (Dubois et al (1998) Faseb J. 12, 1063–1073). Consistent with this, other observations suggest that inflammatory processes may contribute to this disease (Aisen (1997) Gerontology 43, 143–9).

In various further aspects the present invention relates to screening and assay methods and means, and substances identified thereby, especially inhibitors of PGE synthase.

Thus, further aspects of the present invention provide the use of a polypeptide or peptide (particularly a fragment of a polypeptide of the invention as disclosed, and/or encoding nucleic acid therefor), in screening or searching for and/or obtaining/identifying a substance, e.g. peptide or chemical compound, which interacts and/or binds with the polypeptide or peptide and/or interferes with its function or activity or that of another substance, e.g. polypeptide or peptide, which interacts and/or binds with the polypeptide or peptide of the invention. For instance, a method according to one aspect of the invention includes providing a polypeptide or peptide of the invention and bringing it into contact with a substance, which contact may result in binding between the polypeptide or peptide and the substance. Binding may be determined by any of a number of techniques available in the art, both qualitative and quantitative.

In various aspects the present invention is concerned with provision of assays for substances which interact with or bind a polypeptide of the invention and/or modulate one or more of its activities.

One aspect of the present invention provides an assay which includes:

(a) bringing into contact a polypeptide or peptide according to the invention and a putative binding molecule or other test substance; and (b) determining interaction or binding between the polypeptide or peptide and the test substance.

A substance which interacts with the polypeptide or peptide of the invention may be isolated and/or purified, manufactured and/or used to modulate its activity as discussed.

It is not necessary to use the entire proteins for assays of the invention which test for binding between two molecules as above or test for PGE synthase activity (see below). Fragments may be generated and used in any suitable way known to those of skill in the art. Suitable ways of generating fragments include, but are not limited to, recombinant expression of a fragment from encoding DNA. Such fragments may be generated by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments (e.g. up to about 20 or 30 amino acids) may also be generated using peptide synthesis methods which are well known in the art.

The precise format of the assay of the invention may be varied by those of skill in the art using routine skill and knowledge. For example, the interaction between the polypeptides may be studied in vitro by labelling one with a detectable label and bringing it into contact with the other which has been immobilised on a solid support. Suitable detectable labels include $^{35}$S-methionine which may be incorporated into recombinantly produced peptides and polypeptides. Recombinantly produced peptides and polypeptides may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

Determination of the ability of a test compound to interact and/or bind with a PGE synthase polypeptide or fragment may be used to identify that test compound as a candidate for a modulator of PGE synthase activity. Generally, then identification of ability of a test compound to bind a polypeptide or fragment of the invention is followed by one or more further assay steps involving determination of whether or not the test compound is able to modulate PGE synthase activity. Naturally, assays involving determination of ability of a test substance to modulate PGE synthase activity may be performed where there is no knowledge about whether the test substance can bind or interact with the PGE synthase, but a prior binding/interaction assay may be used as a "coarse" screen to test a large number of substances, reducing the number of candidates to a more manageable level for a functional assay involving determination of ability to modulate PGE synthase activity. A further possibility for a coarse screen is testing ability of a substance to affect PGE production by a suitable cell line expressing PGE synthase (either naturally or recombinantly). An assay according to the present invention may also take the form of an in vivo assay. The in vivo assay may be performed in a cell line such as a yeast strain in which the relevant polypeptides or peptides are expressed from one or more vectors introduced into the cell. A still further possibility for a coarse screen is testing ability of a substance to affect PGE production by an impure protein preparation including PGE synthase (whether human or other mammalian). Ultimately, however, a preferred assay of the invention includes determining the ability of a test compound to modulate PGE synthase activity of an isolated/purified polypeptide of the invention (including a full-length PGE synthase or an active portion thereof).

A method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

In a further aspect of the invention there is provided an assay method which includes:

(a) incubating an isolated polypeptide which has PGE synthase activity and a test compound in the presence of reduced glutathione and PGH$_2$ under conditions in which PGE is normally produced; and (b) determining production of PGE.

PGH$_2$ substrate for PGE synthase may be provided by incubation of cyclooxygenase and arachidonic acid, so these may be provided in the assay medium in order to provide PGH$_2$.

Furthermore, PGE synthase catalyses sterospecific formation of 9-keto, 11α hydroxy prostaglandin from the cyclic endoperoxide and so other substrates of PGE synthase may be used in determination of PGE synthase activity, and the effect on that activity of a test compound, by determination of production of the appropriate product.

| Substrate | Product |
|---|---|
| PGH$_2$ | PGE$_2$ |
| PGH$_1$ | PGE$_1$ |
| PGH$_3$ | PGE$_3$ |
| PGG$_2$ | 15 (S) hydroperoxy PGE$_2$ |

-continued

| Substrate | Product |
|---|---|
| PGG$_1$ | 15 (S) hydroperoxy PGE$_1$ |
| PGG$_3$ | 15 (S) hydroperoxy PGE$_3$ |

Thus, a more general aspect of the invention provides an assay method which includes:

(a) incubating an isolated polypeptide which has PGE synthase activity and a test compound in the presence of a cyclic endoperoxide substrate of PGE synthase under conditions in which PGE synthase normally catalyses conversion of the cyclic endoperoxide substrate into a product which is the 9-keto, 11α hydroxy form of the substrate; and (b) determining production of said product.

As noted, the substrate may be any of those discussed above, or any other suitable substrate at the disposal of the skilled person. It may be PGH$_2$, with the product then being PGE.

An inhibitor of PGE synthase may be identified (or a candidate substance suspected of being a PGE synthase inhibitor may be confirmed as such) by determination of reduced production of PGE or other product (depending on the substrate used) compared with a control experiment in which the test compound is not applied.

Product determination may employ HPLC, UV spectrometry, radioactivity detection, or RIA (such as a commercially available RIA kit for detection of PGE). Product formation may be analysed by gas chromatography (GC) or mass spec. (MS), or TLC with radioactivity scanning.

Combinatorial library technology (Schultz, JS (1996) Biotechnol. Prog. 12:729–743) provides an efficient way of testing a potentially vast number of different substances for ability to modulate activity of a polypeptide.

The amount of test substance or compound which may be added to an assay of the invention will normally be determined by trial and error depending upon the type of compound used. Typically, from about 0.1 nM to 10 µM concentrations of a test compound (e.g. putative inhibitor) may be used. Greater concentrations may be used when a peptide is the test substance.

Compounds which may be used may be natural or synthetic chemical compounds used in drug screening programmes. Extracts of plants which contain several characterised or uncharacterised components may also be used.

Other candidate inhibitor compounds may be based on modelling the 3-dimensional structure of a polypeptide or peptide fragment and using rational drug design to provide potential inhibitor compounds with particular molecular shape, size and charge characteristics.

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified as a modulator of polypeptide activity, in accordance with what is disclosed herein, and a substance obtained by a method of the invention, but also a pharmaceutical composition, medicament, drug or other composition comprising such a substance, a method comprising administration of such a composition to a patient, e.g. for treatment (which may include preventative treatment) of inflammation or a cellular growth abnormality or other disease or condition as discussed, use of such a substance in manufacture of a composition for administration, e.g. for treatment of inflammation or a cellular growth abnormality or other disease or condition as discussed, and a method of making a pharmaceutical composition comprising admixing such a substance with a pharmaceutically acceptable excipient, vehicle or carrier, and optionally other ingredients.

A substance identified using as a modulator of PGE synthase activity may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Mimetics of substances identified as having ability to modulate polypeptide activity using a screening method as disclosed herein are included within the scope of the present invention. A polypeptide, peptide or substance able to modulate activity of a polypeptide according to the present invention may be provided in a kit, e.g. sealed in a suitable container which protects its contents from the external environment. Such a kit may include instructions for use.

Further aspects and embodiments of the present invention will be apparent to those skilled in the art. The following experiments provide support for and exemplification by way of illustration of aspects and embodiments of the invention.

All documents mentioned in this specification are incorporated by reference.

Experimental

As noted above, prior to the inventors' work disclosed herein there was no suggestion that the cDNA sequence in the GenBank database labelled as MGST1-L1 (GenBank accession number AF027740) as well as a p53 induced PIG12 (GenBank accession number AF010316 encodes human PGE synthase. Polyak et al. (supra.) noted merely that the PIG12 cDNA appeared to encode another, one might say yet another, microsomal glutathione S-transferase.

The inventors expressed the protein identified by them as PGE synthase (SEQ ID NO: 2) in a bacterial expression system, employing the coding sequence of SEQ ID NO: 1. Following heterologous expression in E. coli, both cytosolic and membrane fractions were prepared. A rabbit antiserum was raised against an internal peptide of PGE synthase and Western blot analysis specifically detected a 15 kDa protein in the membrane fraction from bacteria expressing PGE synthase.

The bacterial membrane and cytosolic fractions were incubated with $PGH_2$ in the presence or absence of reduced glutathione. The products ($PGF_{2\alpha}$, $PGE_2$, $PGD_2$ and 12-HHT) were analyzed by RP-HPLC using UV absorption at 195 nm as well as on line radioactivity detection. The membrane but not the cytosolic fraction was found to possess high glutathione dependent PGE synthase activity (0.25 μmol/min/mg).

A549 cells were used as a model to study cyclooxygenase-2 induction by interleukin-1β. When A549 cells were grown in the presence of interleukin-1β (1 ng/ml) for 24 h a significant induction of the PGE synthase protein was observed using Western blot analysis. Also, the antiserum specifically recognized a 16 kDa protein in commercially available partly purified PGE synthase activity isolated from sheep seminal vesicles.

Material and Methods

Materials

Rabbit anti-human PGE synthase antiserum was raised to the following synthetic peptide: CRSDPDVERSLRAHRN (SEQ ID NO: 3) conjugated with keyhole-limpet hemocyanin (Innovagen, Lund, Sweden). This peptide antigen corresponds to amino acids 59–74 of PGE synthase (note: Cys 68 was replaced with Ser, in case inclusion of Cys interfered with the peptide synthesis).

Horseradish peroxidase-linked donkey anti-rabbit antibody was purchased from Amersham Pharmacia Biotech, England. Film (hyperfilm ECL) was also obtained from the same source. Oligonucleotides were from Kebo laboratory, Sweden. Pfu DNA polymerase was from Stratagene, CA, USA. $PGH_2$ and $3H-PGH_2$ was purchased from Cayman chemical, USA. $PGF_{2\alpha}$, $PGE_2$, $PGD_2$ and 12-HHT was obtained from Biomol, PA, USA. Glutathione and Interleukin-1β were from Sigma-Aldrich, Inc. HPLC solvents were from Rathburn Chemicals, Scotland. Partly purified PGE synthase, isolated from ovine seminal vesicles, was obtained from Oxford Biomedical Research, Inc., MI, USA. The cell line A549 was from Boehringer Ingelheim Biowhittaker, Belgium. Cell culture media and antibiotics were from Gibco BRL, Life Technology, Sweden. Protease inhibitor mixture, Complete™, was obtained from Boehringer Mannheim Scandinavia, Sweden.

Isolation and Cloning of PGE Synthase

The EST clone 143735 with GenBank accession number R76492, has previously been identified as "microsomal glutathione-S-transferase 1-like 1" (MGST1-L1) encoded by GenBank accession number AF027740. The same gene product has also been characterized as "p53 induced PIG12" encoded by GenBank accession number AF010316.

The coding sequence of PGE synthase corresponding to the nucleotide sequence 19 to 477 of the EST clone 143735 (accession number AF027740) was amplified by PCR. Oligonucleotide primers were constructed to incorporate suitable restriction sites (Nde I-Hind III) into the 5' and 3' ends of the product.

Primer 1 (sense): 5'-GAGAGA CATATGCCTGCCCACAGCCTG-3' (underlining is Nde I-site);

Primer 2 (antisense): 5'-GAGAGA AAGCTTCACAGGTGGCGGGCCGC-3' (underlining is Hind III-site).

In both primers GAGAGA are just additional flanking nucleotides.

PCR was performed with 0.2 mM dNTPs, 0.5 µM of the respective primer, 70 ng template, 2.5 U of Pfu polymerase in 1×Pfu buffer (supplied by the manufacturer). The temperature cycles were 45 s at 94° C., 45 s at 60° C. and 45 s at 72° C., repeated 25 times. However, the first denaturing period was 4 min and the last extension period was 10 min. The PCR product was isolated by agarose gel electrophoresis, purified from the gel and cut with Nde I and Hind III.

The resulting product was gel-purified and ligated into the bacterial expression vector pSP19T7LT (Weinander, R., et al.(1995) Biochemical Journal 311, 861–6). Ligated plasmids were transformed into DH5aTM competent cells. Plasmids were isolated from a number of clones and cleaved with NdeI and Hind III followed by agarose gel electrophoresis to confirm the size of inserts. Selected inserts were sequenced on an Applied Biosystems 373A automated DNA sequencer using a dye terminator cycle sequencing kit.

The expression construct containing the correct coding sequence for the PGE synthase was transformed into *E. coli* BL21 (DE3) (that harbored the plasmid pLys SL (Studier, F. W. (1991) Journal of Molecular Biology 219, 37–44). Glycerol stocks were prepared and stored frozen at −70° C. for subsequent use as starting material for the expression experiments.

Expression in *E coli*

Small aliquots (1–2 µl) of bacterial glycerol stock were grown in 2×YT overnight at 37° C. The cultures were diluted 1:100 into 2 l of Terrific Broth medium containing ampicillin (75 µg/ml) and chloramphenicol (10 µg/ml) in a 5 l flask placed in a thermostated water bath. The culture was oxygenated by air bubbling and grown until the $OD_{600}$ was 0.4–1.2. At this point expression was induced by the addition of 1 mM isopropyl β-D-thiogalactopyranoside, the temperature was switched to 30° C. and the culture allowed to grow for another 4 h.

Thereafter, cells were pelleted and resuspended in 100 ml TSEG buffer (15 mM Tris-HCl, pH 8.0, 0.25 M sucrose, 0.1 mM EDTA, 1 mM glutathione). Lysozyme was added to a final concentration of 0.2 mg/ml, and the mixture was gently stirred for 30 min at 4° C. Then the cells were lysed by six 30 s sonication pulses from a MSE Soniprep 150 sonifier at 40–60% of maximum power. Cell debris was removed by centrifugation at 5000×g for 10 min. The supernatant was then centrifuged at 250,000×g for 1 h and the membrane pellets were finally resuspended in 10 mM potassium phosphate, pH 7.0, 20% glycerol, 0.1 mM EDTA, 1 mM glutathione. Total protein concentration was determined by the Coomassie protein assay according to the manufacturer's instructions (Bio-Rad).

SDS PAGE and Western Blotting

Samples were diluted and boiled for two min in SDS-containing sample buffer (Laemmli, U. K. (1970) Nature 227, 680–5). Proteins were separated through 14% polyacrylamide gels (Novex) and electroblotted (Towbin, H., et al.(1979) PNAS USA 76, 4350–4) onto PVDF (Pall) membranes. Transfer efficiency was visualized using pre-stained standards (Novex). Membranes were then soaked for 1 h at 25° C. in Tris-buffered saline (100 mM Tris-HCl, pH=7.5, 150 mM NaCl) containing 0.1% (v/v) Tween and 5% (w/v) non-fat dried milk. The membrane was subsequently washed twice in 0.1% T-TBS followed by 1 h incubation at 25° C. with the indicated antiserum (1:2000 dilution) in 0.05% (v/v) T-TBS and 2% (w/v) non-fat dried milk. Following several washing steps (2×1 min, 1×15 min and 3×5 min, the blot was incubated for 1 h at 25° C. with a horseradish peroxidase-linked donkey anti-rabbit antibody (1:2000 dilution) in 0.05% (v/v) T-TBS and 2% (w/v) non-fat dried milk. The washing steps were repeated and subsequently enhanced chemiluminescence detection was performed according to the manufacturer's instructions (ECL plus, Amersham Pharmacia Biotech, England).

Cell Culture

A549 cells were cultured in RPMI 1640 supplemented with heat-inactivated fetal bovine serum (10%), fungizone (2.5 µg/ml), penicillin (100 U/ml), streptomycin (100 µg/ml), at 37° C. in an atmosphere of 5% $CO_2$. Cells were seeded at a concentration of $0.15×10^6$/ml in 75 cm² flasks. After three days, confluence was reached and cells were washed in PBS twice, then detached using 1.5 ml 1×Trypsin/EDTA solution (GibcoBRL) for 15 min at 37° C. in an atmosphere of 5% $CO_2$. Thereafter 3 ml medium was added to quench the trypsin and cells were further diluted and reseeded at appropriate number/cm² as just described.

In order to investigate the effect of IL-1β on PGE synthase expression in A549 cells, $1×10^6$ cells in 5 ml medium were plated in 25 cm² flasks and incubated for 24 h. Subsequently, the cells were washed in PBS three times followed by addition of 5 ml RPMI 1640 medium containing fetal bovine serum (2%), β(1 ng/ml) and incubated for another 24 h. For harvest, cells were washed in PBS twice, trypsinated in 0.5 ml 1×Trypsin/EDTA solution for 15 min at 37° C. 1 ml culture media was added and cells were centrifuged at 500×g for 10 min followed by two washes in 1 ml PBS. Cells were resuspended in 50 µl homogenization buffer consisting of potassium phosphate buffer (0.1 M, pH=7.4) and 1×Complete™ protease inhibitor cocktail. Samples were sonicated 2×10 s, then 50 µl boiling 2×Laemmli buffer was added and the sample was boiled for additional 2 min.

PGE Synthase Enzyme Assay

The protein sample was diluted in potassium inorganic phosphate buffer (0.1 M, pH=7.4) containing 2.5 mM reduced glutathione. The reaction (total volume =100 µl) was started by the addition of 10 µM $PGH_2$ with or without 0.1 µCi 3H $PGH_2$ and terminated with 60 µl acetonitrile/HCl, lowering the pH to 3.2. In order to determine the formation of either $PGF_{2α}$, $PGE_2$ or $PGD_2$, an aliquot (60 µl) was analyzed by reverse-phase-HPLC combined with UV detection (195 nm) and/or radioactivity detection using an online β-RAM detector (Inus System, Inc.). The reverse-phase HPLC column was Nova-Pak C18 (3.9×150 mm, 4 µm particle size) obtained from Waters. The mobile phase was water, acetonitrile and trifluoroacetic acid (70:30:0.007, by vol) with a flow rate of 1 ml/min.

For analysis of 12-HHT, a mobile phase of methanol, water and acetic acid (70:30:0,01, by vol) was used and UV detection at 236 nm. The amounts of produced $PGE_2$ and 12-HHT were quantified by integration of the areas under the eluted peaks at 195 and 236 nm, respectively.

Results

Identification of PGE Synthase

The amino acid sequence of human PGE synthase (SEQ ID NO: 2) has amino acid sequence identity of 38% with MGST1. In addition, MGST1 and PGE synthase display similar hydropathy profiles and high pI:s (>10).

Expression of PGE Synthase

PGE-synthase was expressed using a bacterial expression system. In order to demonstrate protein expression, a peptide antiserum was raised against PGE synthase (aa segment 59–74).

Both the membrane and cytosolic fractions from bacteria expressing PGE synthase were analyzed by SDS-PAGE and Western blot. As control, the membrane fraction from bacteria expressing ratMGST1 was included. In all lanes, 5 μg of total proteins were analyzed. Results were obtained using antipeptide antiserum against PGE synthase, corresponding preimmune serum, and the antipeptide antiserum diluted in the presence of $10^{-6}$ M peptide antigen. The exposure time was 2 min.

The antiserum recognized a 15 kDa band in the membrane fraction from bacteria expressing PGE synthase. This band was not found in the corresponding cytosolic fraction. Furthermore, the antiserum did not recognize ratMGST1 expressed using the same expression system.

The detection of PGE synthase was specific since antiserum diluted in the presence of $1\times10^{-6}$ M antigen (peptide) lost the capability to detect PGE synthase.

Prostaglandin E Synthase Activity

The membrane fraction (0.02 mg total protein/ml) isolated from bacteria expressing PGE synthase was incubated for 2 min in the presence of $PGH_2$ (10 μM including 1 μCi 3H $PGH_2$) and reduced glutathione (2.5 mM).

Reverse-phase HPLC chromatograms were plotted for the products formed after incubations with $PGH_2$ (plotting counts per minute (CPM) against time in minutes).

FIG. 1A shows results obtained with PGE synthase membrane fraction mixed with stop solution.

FIG. 1B shows results obtained with buffer.

FIG. 1C shows results obtained with PGE synthase membrane fraction. The material in the experiments for which results are shown in FIG. 1B and FIG. 1C were incubated for 2 min prior to addition of stop solution. Products were detected using radioactivity detection. The first 20 min represents isocratic elution using water, acetonitrile and trifluoroacetic acid (70:30:0.007, by vol) as mobile phase with a flow rate of 1 ml/min. Then a linear gradient was applied from 100% mobile phase to 100% methanol over a 10 min period, which was sustained for the rest of the run.

FIG. 1C shows the RP-HPLC profile of radioactive labeled products formed under these conditions. One major peak is produced eluting at 12.3 min corresponding to the elution time of synthetic $PGE_2$. The material of this peak was collected, derivatized and analyzed by GC/MS confirming its identity as $PGE_2$. A minor peak was also produced which eluted at 31.5 min, corresponding to the retention time of 12-HHT.

The non-enzymatic formation of these products is shown in FIG. 1B. In this chromatogram the peak corresponding to $PGE_2$ accounts for less than 25% of that formed in the presence of membranes from bacteria expressing PGE synthase. Instead, the major product formed corresponds to 12-HHT eluting at 31.5 min as well as another minor peak with a retention time of 14.9 min, corresponding to the retention time of $PGD_2$. The chromatogram in FIG. 1A shows the zero time incubation when substrate was added to buffer containing the membrane fraction pre-mixed with stop solution. Little $PGE_2$ was detected and the major product peak corresponded to the retention time of 12-HHT.

The $PGE_2$ formation (FIG. 1C) was abolished if the membrane was boiled for 2 min prior to incubation, demonstrating the enzymatic nature of catalysis. Also, no PGE synthase activity was observed using the membrane fraction obtained instead from bacteria expressing ratMGST1. If the membrane fraction was treated with N-ethylmaleimide (1 mM) for 5 min prior to incubation, the enzyme activity was abolished. No activity was detected in the cytosolic fraction from bacteria expressing PGE synthase. Moreover, no PGE synthase activity was observed in microsomes obtained from Sf9 cells expressing MGST2.

FIG. 2 demonstrates the production of $PGE_2$ as a function of protein concentration. In this experiment the various dilutions of the membrane fraction obtained from bacteria expressing PGE synthase were incubated in the presence of $PGH_2$ (10 μM) and GSH (2.5 mM) for 2 min. The $PGE_2$ formation was analyzed and quantified by RP-HPLC and UV detection at 195 nm as described in Materials and Methods above.

A linear relationship was found using protein concentrations up to 0.015 mg/ml. Thereafter the slope rapidly declines due to almost complete conversion of added $PGH_2$ into $PGE_2$.

Figure 3:
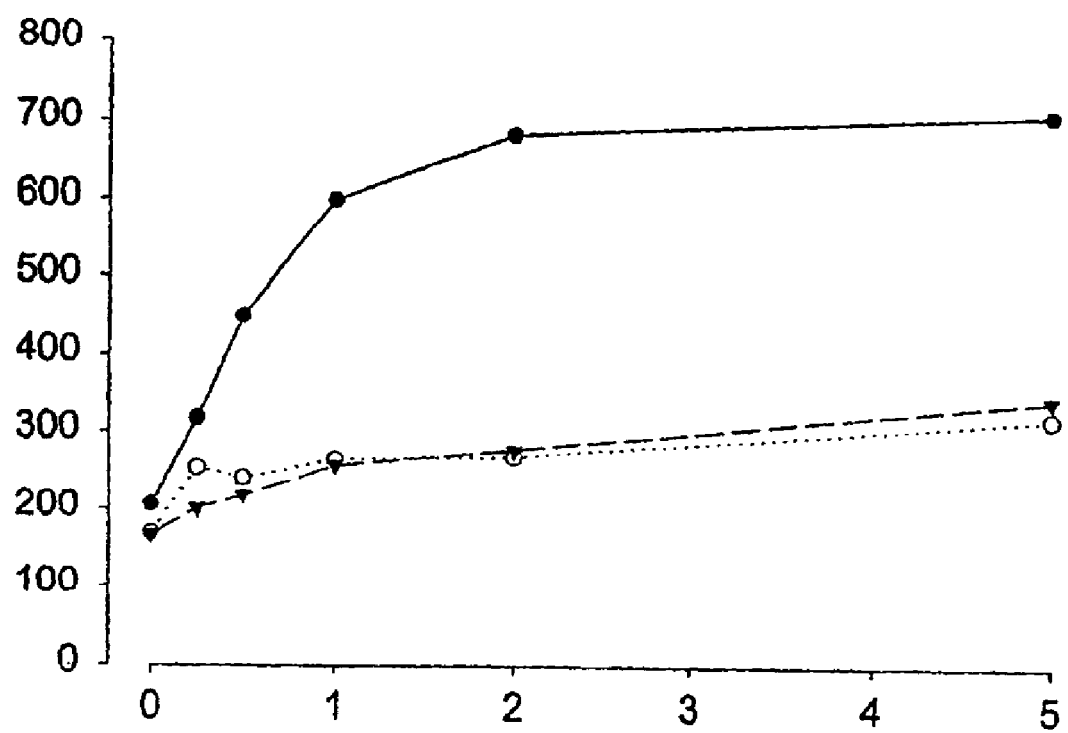
FIG. 3 shows a time course for $PGE_2$ formation, amount of $PGE_2$ in pmol being plotted against time in minutes. Filled circles are for PGE synthase incubated with glutathione; open circles are for PGE synthase without glutathione; filled triangles are for buffer with glutathione.

FIG. 3 demonstrates the time function of the $PGE_2$ production after incubation of the membrane fraction (0.02 mg/ml) with $PGH_2$ (10 μM) in the presence or absence of GSH (2.5 mM). The membrane fraction obtained from bacteria expressing PGE synthase (0.02 mg/ml) was incubated with $PGH_2$ for the indicated times in the presence (filled circles) or absence (open circles) of glutathione. Filled triangles represent non-enzymatic (buffer only) $PGE_2$ formation after incubation with $PGH_2$. The product formation was analyzed by RP-HPLC and $PGE_2$ was detected and quantified using UV absorbance at 195 nm.

A linear relationship is obtained during the first 60s of incubation. Thereafter the slope of the curve declines due to substrate depletion.

FIG. 3 also shows that the activity is dependent on the presence of glutathione. The specific activity under linear conditions (substracting background formation) was 600 pmol/1.2min/0.002 mg membrane fraction (i.e. 250 nmol/min/mg).

Induction of PGE Synthase by IL-1β

A549 cells have been used to study cox-2 induction and have also been reported to significantly increase their $PGE_2$ release following treatment with interleukin-1β. In order to investigate whether or not PGE synthase may also be regulated by this cytokine, A549 cells were cultured for 24 h in the presence of 1 ng/ml IL-1β. Normal cells as well as cells treated with IL-1β were subsequently analyzed for PGE synthase expression by SDS-PAGE followed by Western blotting.

Total protein corresponding to $0.2\times10^6$ cells grown for 24 h in the presence (1 ng/ml) or absence of IL-1β was fractionated by SDS-PAGE and transferred to PVDF membrane. The membranes were incubated using either PGE synthase antiserum or PGE synthase antiserum containing the antigenic peptide ($10^{-6}$ M). Also analyzed was the commercial available, partly purified, PGE synthase from sheep seminal vesicles (6 μg) as well as the membrane fraction from bacteria expressing human PGE synthase (5 μg).

PGE synthase was induced by IL-1β. In the lane loaded with IL-1β treated cells, a 15 kDa band appeared comigrating with the expressed PGE synthase in bacteria. The recognition was lost if antiserum was mixed with the antigenic peptide (1 μM), demonstrating specific detection of PGE synthase in A549 cells treated with IL-1β. Significantly lower amounts of PGE synthase were detected in non-treated A549 cells.

Identification of an Immunoreactive 16 kDa Protein in Partly Purified PGE Synthase Derived From Ovine Seminal Vesicles The commercially available impure PGE synthase preparation, partly purified from ram seminal vesicles, was tested for cross reactivity to human PGE synthase antiserum.

From the results of the Western blotting, it was evident that a 16 kDa protein band appeared in the lane loaded with 6 μg of this sample. The band was lost using the peptide absorbed antiserum suggesting specific recognition. The protein differs somewhat in size and appears more diffuse, which may suggest some kind of posttranscriptional modification.

PGE Synthase Activity Assay

Earlier studies have demonstrated that prostaglandins can be separated by RP-HPLC and detected by UV spectrophotometry (Terragno et al., (1981) Prostaglandins 21(1), 101–12; Powell (1985) Anal. Biochem. 148(1), 59–69). The molar extinction coefficient of PGE2 is 16,500 at 192.5 nm (Terragno et al., (1981) Prostaglandins 21(1), 101–12). The differences between the absorbance at 192.5 nm and 195 nm was marginal (Terragno et al., (1981) Prostaglandins 21(1), 101–12). However, our results using the RP-HPLC conditions (described below) demonstrated a significantly more stable baseline, with less noise at the higher wavelength. The main products of PGH2 are PGF2α, PGE2 and PGD2. Using the described RP-HPLC conditions, the retention times were 19.0, 23.8 and 28.6 minutes for PGF2α, PGE2 and PGD2, respectively. In order to obtain an internal standard we have tested 11β-PGE2 and 16,16-dimethyl PGE2. The latter compound was too hydrophobic and could not be used in the described isocratic system. In contrast, 11β-PGE2 eluted with a retention time of 25.3 min with almost baseline separation from PGE2. In order to investigate the UV-absorbance relationship between 11-β $PGE_2$ and $PGE_2$, equal amounts (quantified by GC-MS) were analyzed by RP-HPLC and analyzed by UV-absorbance at 195 nm. The two compounds showed identical UV-absorbance properties. In order to test the recovery and reproducibility of solid phase extraction, known amounts of 11-β $PGE_2$ and $PGE_2$ were diluted in sample buffer and acidified by adding the stop solution (containing no iron chloride) followed by the addition of acetonitrile (33% final conc) and subjected to analysis (10% (v/v) of total sample). Alternatively, after the addition of stop solution, the sample was extracted by solid phase extraction and the corresponding fraction (10% (v/v) of total sample) was then analysed. The amounts of 11-β $PGE_2$ and $PGE_2$ before and after extraction were compared and the recovery was estimated to be 85–90%.

In order to quantify $PGE_2$, a standard curve of $PGE_2$ was made. The curve was linear over the range from 0.9 pmol to 706 pmol ($R^2=0.9997$, k=0.0012). For quantification we routinely use both the external standard as well as the internal standard technique, the latter method accounting also for losses during preparation.

Some difficulties may be encountered when assaying PGE synthase with PGH2. The substrate is very labile and decomposes non-enzymatically, with a half-life of about 5 min at 37° C., into a mixture of PGE2 and PGD2 with a E/D ratio of abut 3 (Hamberg et al., (1974) Proc. Natl. Acad. Sci. (USA) 71, 345–349; Nugteren and Christ-Hazelhof (1980) In Adv. in Prostaglandin and Thromboxane Res. 6, edited by B. Samuelsson, P. W. Ramwell, and R. Paoletti. Raven Press: NY, 129–137). Also, the PGE synthase catalysis is very fast, which is why substrate depletion easily can occur within seconds thus preventing a quantitative analysis. After the reaction has been terminated, any remaining PGH2 must also rapidly be separated from the products in order not to interfere with the results. To cope with these properties of the substrate, the assay may be performed as follows.

In order to minimize non-enzymatic production of $PGE_2$, the substrate ($PGH_2$) was always kept on $CO_2$-ice (−78° C.) until use and the enzyme reaction was performed at 0° C. in the presence of PGH2 and reduced glutathione (GSH). A stop-solution was used, containing $FeCl_{21}$ which converted any remaining $PGH_2$ into HHT (Hamberg and Samuelsson (1974) Proc. Natl. Acad. Sci. (USA) 71(9), 3400–4). Also, the products are much more stable in organic solvents (Nugteren and Christ-Hazelhof (1980) In Adv. in Prostaglandin and Thromboxane Res. 6, edited by B. Samuelsson, P. W. Ramwell, and R. Paoletti. Raven Press: NY, 129–137), so we immediately extracted the sample after termination by solid phase extraction and kept the eluate in acetonitrile.

Assay Method

Protein samples were diluted in potassium inorganic phosphate buffer (0.1M, pH 7.4) containing 2.5 mM reduced glutathione (GSH). 4 μl $PGH_2$, dissolved in acetone (0,284 mM) was added to eppendorf tubes and kept on $CO_2$-ice (−78° C.). Prior to the incubation, both the substrate and samples were transferred onto wet-ice (or 37° C.) for 2 min temperature equilibration. the reaction was started by the addition of the 100 μl sample to the tubes containing $PGH_2$. The reaction was terminated by the addition of 400μl stop solution (25 mM $FeCl_2$ 50 mM citric acid and 2.7 μM 11-β $PGE_2$), lowering the pH to 3, giving a total concentration of 20 mM $FeCl_2$, 40 mM citric acid and 2.1 μM 11-β $PGE_2$. Solid phase extraction was performed immediately using C18-chromabond columns. The samples were eluted with 500 μul acetonitrile and thereafter 1 ml $H_2O$ was added. In order to determine the formation of $PGE_2$ and 11-β $PGE_2$, an aliquot (150 μl) was analyzed by RP-HPLC, combined with UV detection at 195 nm. The reverse-phase HPLC column was Nova-Pak C18 (3.9×150 mm, 4 μm particle size) obtained from Waters and the mobile phase was water, acetonitrile and trifluoroacetic acid (72:28:0.007, by vol). The flow rate was 0.7 ml/min and the products were quantified by integration of the peak areas.

Discussion

MGST1-L1 was identified as a homologue to MGST1 exhibiting similarities both on the sequence level (38% amino acid identity) as well as structural properties (hydrophobicity profile).

MGST1-L1 was expressed using a bacterial expression system. When tested for PGE synthase activity, membranes from bacteria expressing MGST1-L1 exhibited a significant PGE synthase activity (0.25 μmol/min/mg) corresponding to the highest levels of normally occurring PGE synthase activity, i.e. in microsomes isolated from sheep seminal vesicles (Moonen, P., et al. (1982) Methods in Enzymology 86, 84–91) and rat ductus deferens (Watanabe, K., et al. (1997) Biochemical & Biophysical Research Communications 235, 148–52). In fact, estimating that 1% of the bacterial membrane protein is MGST1-L1, the deduced specific activity becomes 25 μmol/min/mg corresponding to a Kcat/Km in the $10^6$ M-1S-1 range. Such high Kcat/Km values are hallmarks of extremely efficient enzymes (Fersht, A. (1985) Enzyme Structure and Mechanism (W. H. Freeman & Co., New York) Considering the short half-life of PGH$_2$ and the existence of competing pathways it makes sense that a physiologically relevant activity is highly efficient.

These results provide indication that MGST1-L1 is human PGE synthase, Western blot analysis confirmed successful expression of the protein and also that PGE synthase protein expression was upregulated in A549 cells (a human lung adenocarcinoma cell line) following IL-1β treatment. A549 cells have been used by many investigators to study the regulation of cox-2 and related enzymes such as cytosolic phospholipase A2. The results agree with published data demonstrating the upregulation of cox-2 and the several-fold increase of PGE$_2$ biosynthesis in response to interleukin-1β treatment of A549 cells (Huang, M., et al. (1998) Cancer Res. 58, 1208–1216; Mitchell, J., et al.(1994) British J. of Pharmacol. 113, 1008–1014). Combined with these findings on cox-2, the data suggest that PGE synthase and cox-2 are co-regulated and that PGE$_2$ biosynthesis may be dependent on the presence of both these enzymes. In accordance, an inducible PGE synthase activity has also been described in lipopolysaccharide-stimulated rat peritoneal macrophages, which coincides with cox-2 expression and changes the product formation in favour of PGE$_2$ (Naraba, H., et al.(1998) Journal of Immunology 160, 2974–82; Matsumoto, H., et al.(1997) Biochemical & Biophysical Research Communications 230, 110–4). The induction of PGE synthase (PIG12) following p53 expression in a colorectal cancer cell line (DLD-1) (Polyak, K., et al. (1997) Nature 389, 300–305) may also be of importance for understanding the role of cox and PGE synthase in cancer and apoptosis. Cyclooxygenase-2 has also been implicated in colon cancer through the beneficial effects observed by various NSAIDs on cancer growth (Dubois, R., et al.(1998) Faseb J. 12, 1063–1073).

In summary, the first microsomal glutathione dependent PGE synthase has been identified and characterised and demonstrated to be upregulated by the proinflammatory interleukin-1β in a lung cancer cell line. This cytokine also upregulates cox-2 and cellular capacity to produce PGE$_2$. This provides PGE synthase as a novel target for drug development in various areas, including inflammation, cancer and apoptosis, as discussed already above.

What is claimed is:

1. An isolated and pure polypeptide which is a PGE synthase and which comprises the amino acid sequence of SEQ ID NO. 2.

2. An isolated and pure polypeptide which is a PGE synthase and which consists of an active portion of SEQ ID NO:2 wherein said active portion comprises amino acids 30–152 of SEQ ID NO. 2.

3. An isolated and pure polypeptide which is a PGE synthase and which consists of an active portion of SEQ ID NO:2 wherein said active portion comprises amino acids 1–130 of SEQ ID NO. 2.

4. An isolated and pure polypeptide which is a PGE synthase and which consists of an active portion of SEQ ID NO:2 wherein said active portion comprises amino acids 30–130 of SEQ ID NO. 2.

5. The polypeptide according to claim 1 fused to a heterologous sequence of amino acids.

* * * * *